United States Patent [19]
Altner et al.

[11] Patent Number: 5,293,865
[45] Date of Patent: Mar. 15, 1994

[54] CODING FOR AN ANESTHETICS DEVICE

[75] Inventors: Ulrich Altner, Bad Segeberg; Claus-Dieter Brandt; Wilfried Buschke, Lubeck; Wolfgang Falb, Klein Wesenberg; Gotz Kullik; Carl F. Wallroth, both of Lubeck, all of Fed. Rep. of Germany

[73] Assignee: Dragerwerk AG, Lubeck, Fed. Rep. of Germany

[21] Appl. No.: 590,212

[22] Filed: Sep. 28, 1990

Related U.S. Application Data

[63] Continuation-in-part of Ser. No. 330,115, Mar. 29, 1989, abandoned.

[30] Foreign Application Priority Data

Apr. 22, 1988 [DE] Fed. Rep. of Germany ....... 3813520

[51] Int. Cl.⁵ .................... A61M 15/00; A61M 16/10; F23D 11/00; F23D 14/00
[52] U.S. Cl. .................... 128/203.12; 128/203.16; 128/203.26; 128/202.27; 261/39.1; 261/DIG. 65; 261/96; 261/99; 261/105
[58] Field of Search .................... 128/203.12, 203.16, 128/203.17, 203.25, 203.26, 203.27, 202.27; 261/39.1, DIG. 65, 96, 99, 105

[56] References Cited

U.S. PATENT DOCUMENTS

| | | | |
|---|---|---|---|
| 3,741,208 | 6/1973 | Jonsson et al. | 128/204.21 |
| 3,831,599 | 8/1974 | Needham | 128/203.12 |
| 4,058,120 | 11/1977 | Caparrelli et al. | 128/203.12 |
| 4,215,409 | 7/1980 | Strowe | 128/203.14 |
| 4,345,612 | 8/1982 | Koni et al. | 128/203.14 |
| 4,622,976 | 11/1986 | Timpe et al. | 128/203.12 |
| 4,693,853 | 9/1987 | Falb et al. | 128/203.25 |
| 4,770,168 | 9/1988 | Rusz et al. | 128/203.14 |
| 4,825,860 | 5/1989 | Falb et al. | 128/203.12 |
| 4,883,049 | 11/1989 | McDonald | 128/203.12 |
| 4,905,685 | 3/1990 | Olsson et al. | 128/203.12 |

FOREIGN PATENT DOCUMENTS

2193642 2/1988 United Kingdom ........... 128/203.12

Primary Examiner—Edgar S. Burr
Assistant Examiner—Kimberly L. Asher
Attorney, Agent, or Firm—McGlew and Tuttle

[57] ABSTRACT

An anesthetics monitoring device includes an anesthetic vaporizer, from which the anesthetic can be supplied to a setting device supplying dosed amounts of anesthetic to an anesthetics device for dispensing the anesthesia to a patient. The device has a coding for the unmistakable assignment of the setting device to the type of anesthetic used. An automatic recognition of the anesthetic used and a setting to a metering and control unit for dispersing the anesthetic is guaranteed. Any incorrect metering and incorrect setting is prevented. For this purpose, the coding is brought into an operative connection with a receiver provided between the setting device and the anesthetics dispersing device. The receiver is equipped with a scanning apparatus which is connected to the metering and control dispensing unit by means of signal transfer lines.

11 Claims, 4 Drawing Sheets

CODING FOR AN ANESTHETICS DEVICE

REFERENCE TO COPENDING APPLICATION

This is a continuation-in-part Application of Ser. No. 330,115 filed on Mar. 29, 1989. Abandoned.

BACKGROUND OF THE INVENTION

1. Field of the Invention

The invention relates to an anesthetics device with an anaesthetic vaporizer which supplies an anaesthetic to another device. The vaporizer and its connection to the anesthetics device are known from U.S. Pat. Nos. 4,693,853 and 4,825,860 respectively. a similar anesthetics device is known from German patent No. 35 23 947. The vaporizer has a setting adjustment which supplies dosed amounts of anaesthetic to fresh gas and then to the anesthetics device, and the vaporizer according to the invention has a coding for the unmistakable assignment of the type and concentration of anesthetic used.

In the known anesthetics device a storage container for an anaesthetic is connected to a setting device wherein the storage container engages with the setting device by means of appropriate code pins so that a dosing of the anaesthetic is adjusted to the respective physical properties of the anaesthetic influencing the dosing. The vaporizer and the setting device are connected to an anesthetics applicator, so that the dosed anaesthetic can be supplied to the anesthetics applicator. For an appropriate use of the anesthetics device, the anaesthetic required for the respective anesthetics does actually have to be connected to the pertaining vaporizer and the setting means. In addition, during an anesthetics procedure it is occasionally necessary to change the anesthetic. For this purpose either the vaporizer has to be replaced by another one or, if several vaporizers are connected to the anesthetics device, the vaporizer has to be switched. Herein it is imperative for the operator to ascertain that the desired vaporizer is actually connected and activated. This requires increased attention by the anesthesiologist, which cannot always be continuous, e.g. during applications of longer duration. There is a possibility of controlling the supplied anaesthetic by means of a meter, but only very complex meters have the capability of determining the kind of anesthetic from the metering itself and of choosing the corresponding calibration curve for the indication. More simple meters require manual switching to the kind of anaesthetic used, which can lead to incorrect dosing if an accidental switching error or an omitted adjustment to the new anaesthetic occurs.

SUMMARY OF THE INVENTION

The invention provides an anesthetic device with a simple means for the automatic recognition of the type of anesthetic used and the setting of the concentration at the moment when the vaporizer is connected to the anesthetics metering and control device. This information is fed into the respective metering and controlling device for the control of the anesthetics device to avoid incorrect metering and incorrect setting, and also to create the prerequisites for an automatic adherence to the desired concentration of the anesthetic.

The device for transmitting the type and concentration of anesthetic can be incorporated with the connection between the vaporizer and the anesthetics device. The anesthetic device is equipped with a scanning device for the identification of the code of the vaporizer and it is connected to a metering and control unit by means of signal transfer lines.

An advantage of the invention is that each of the anaesthetic or encoded vaporizers with the respective setting device can be supplied or encoded with information about the type of anesthetic, the possible setting range for the concentration and further data specifically referring to anesthetics. The attempt to connect an anesthetic vaporizer with improper contents or a concentration ratio not desired can either be prevented or the misoperation can be indicated.

Compatibility with vaporizers of similar design, which do not yet have the coding according to the invention is advantageously possible. Any missing coding results in an alarm at the control unit indicating special care is needed, thus stressing their exceptionally advantageous character when in use.

The coding elements are arranged in a simple manner on the setting device and there is also the possibility of retrofitting the existing devices not having these elements, with little effort.

The metering and control unit receives the information as to the type and concentration of anesthetic used. The information on the calibration curve, range of allowable concentration ratios and other information for each specific anesthetic is or can be stored in the metering and control unit. When the metering and control unit receives the information on the type of anesthetic used all stored information on that anesthetic is available and may be displayed if desired. Upon receiving information on the concentration ratio selected on the vaporizer, the metering and control unit checks to insure that the ratio is within the allowable range and can either issue a warning or prevent use if the ratio is outside the acceptable range. The metering and control device can also be interfaced with the mixing means associated with the setting device on the vaporizer, possibly by means of a gear connection, or an additional setting device to control the concentration ratio further. Here, the desired concentration value is entered into the metering and control device and then the setting device of the vaporizer or the additional setting device is adjusted to cause the overall concentration ratio to meet the desired value.

Also because of the influence of atmospheric pressure and gas temperature, compensation of the setting device may be needed. This compensation can be calculated for the chosen anesthetic by the metering and control unit, and the amount of compensation needed is displayed or the setting device is adjusted if the proper interfaces are present.

The metering and control unit switches to the proper calibration curve for the respective anesthetic either automatically or the range is controlled by manual operation. Therefore an incorrect range due to mistake or forgotten switching and therefore the indication of incorrect concentration parameters are prevented.

Of the various embodiments of coding, it has proven to be especially effective to provide coded coupling elements between the vaporizer and the anesthetics device. The coupling elements are provided with several recesses and form parts of various shapes and sizes. One of the coupling elements can e.g. be arranged on a support on the anesthetics device, in which the vaporizer is hung and coupled. Herein one or several form parts or recesses on the support on the anesthetic device engage onto corresponding receiving recesses or form parts on the vaporizers, the outer shape of the form parts being adjusted to the inner shape of the recesses. The form and execution of recesses and form parts can prevent an unauthorized coupling of a vaporizer to the anesthetics device, i.e., a vaporizer with four form parts cannot be connected to a coupling element with only three recesses. As the fourth form part does not find a corresponding recess in the coupling element, a fitting mounting is not possible. The coupling element recognizes this mistaken attempt by means of signal emitters on the form parts of recesses and sends a respective message to the metering and control unit.

A simple implementation of the above idea is realized if the recesses are borings of various depth engaging with corresponding pins, and depending on the depth of engagement an electrical switch or a light barrier can be used as a signal transmitter. Such a pin coding allows the arrangement to either activate the electrical switches or to leave them inert, depending on the engagement depth of the pins into the borings, their respective signals being interpreted as either on-position or off-position. By this means a simple digital pin coding becomes possible. The variation of the coding possibilities can be combined with the number of the pins as well as with their varying engagement depth.

In addition to the above mechanical codings an optical coding by means of an arrangement of light sources, receivers and/or reflectors is advantageous. Herein the coding can be translated into a specific pattern of these light devices, which can be arranged on the anesthetic device and on the setting means. The code depending on the number of light beams is sent to a receiver. It is decoded and passed on as respective information to the metering and control unit. Such a reflex coding has the advantage that it works touchless, can be realized with simple means and that the mechanical effort is kept small.

A further alternative is a magnetic coding on the contact surface between the anesthetic device and the vaporizer. Advantageously, the scanning device is a magnetic strip reader. During the coupling of the vaporizer and the setting device to the anesthetics device a magnetic strip is positioned over the magnetic strip reader. In order to read the data saved on the magnetic strip, it is pulled over the reader head of the magnetic strip reader by means of a tongue provided for this purpose. The entered data is passed on to the control unit.

If, in addition to the type of anesthetic coding, a coding of information with regard to the setting itself in the setting device is desired to make it further controllable, a digitally coded strip which is mounted to the outer edge of a disc-shaped handwheel provided on the setting device can be used. Its coded markings are read by an optical scanning device by means of reflected light and the information is read and fed into an interpretation unit, which passes this information on to the metering and control unit. The coding can also advantageously contain information on the kind of anesthetic, the zero-position and the operating positions of the vaporizer. Alternatively, the setting can be detected by a transmitter of the angle of rotation on the setting device, such as a handwheel. The setting of the handwheel must correspond to a set value, which does not only influence the vaporizer itself but which is also transferred to the metering and control unit by means of scanning. Herein the set value can, depending on the embodiment, either serve to control a manual switching of the metering and control unit to the respective anesthetic or to execute this switching automatically. The scanning of the zero position allows control so that, during the operation of the anesthetics device, the activation of the vaporizer is not accidentally forgotten and that the vaporizer is stopped when not in use. If several vaporizers are connected to an anesthetics device, the scanning of the zero position serves to assure that only one vaporizer is activated at a time and to receive information on the individuality and kind of the anesthetic in use. During operation the information on concentration provided with regard to the orientation of the handwheel is compared to the actual values of the metering device and a warning is given as soon as an unacceptable deviation occurs between the two. Herein the tolerance can be adjusted to the parameter of the set concentration according to experimental values and programmed in the metering and control unit.

In the case that several setting devices with their respective codes are connected to the anesthetics device, the vaporizers which are not used are blocked by a stopper and the vaporizer to be used is opened. The opened vaporizer is made known to the metering and control unit by means of the light barriers devices positioned on of the stopper.

For a further simplification of the interpretation of the codes, a code memory is incorporated into the metering and control unit, and preferably all authorized codes are stored in the memory. When a vaporizer is connected, its code signals are compared with the stored codes or authorized code patterns in the memory by means of a comparator. The vaporizer is checked to determine whether the delivered code is one of the stored codes. Thus control is simplified when several anesthetics are used.

In a further embodiment a part of the code memory of the control unit is arranged in the setting device of the vaporizer. Preferably a permanent memory, e.g. EPROM, is used and contains all vaporizer-relevant data such as calibration, anesthetics code and also production and service information. If the setting of the setting device is e.g. registered by means of the angle of rotation of a transmitter, the signal can be combined with the vaporizer-relevant data in a microprocessor which is also arranged in the setting device. The microprocessor has e.g. an operative connection with the metering and control unit by means of a signal line. One advantage achieved through this embodiment is that now additional vaporizer-relevant, individual calibration parameters can be included in the check of the concentration ratio predetermined by the setting device and the metering and control device.

With regard to the memory element, it may consist of a digitally structured array of storage elements, in which is stored the information of desired concentration of volatile anesthetics in correlation to the position of the setting device. Furthermore, the memory element contains allowable combinations of codes activated by the connecting elements or combinations of light signals by way of encoded arrays of AND- and OR-gates within the memory. Now, when a specific vaporizer containing halothane is put onto the support, a pin may be depressed and the others may maintain their position. An electrical signal is delivered by a micro-switch which is built inside the support and adjacent to each pin. Now, the depressed pin activates its respective micro-switch and the other two are not activated. A corresponding combination of electrical signals is given to the corresponding AND- and OR-gates and is recognized by the memory as being an allowed combination and is being addressed to halothane. A display is activated showing that an allowable vaporizer containing halothane is being used. Corresponding activities are initiated when light signals are used.

Any change of information with regard to the memory may be performed by exchanging an erasable PROM (Programmable Read only Memory) or by inserting new information into memory by means of an external keyboard.

Accordingly, it is an object of the invention to provide an improved apparatus for monitoring the dispensing of an anesthetic which includes an anesthetic device connectable to an anesthetic vaporizer with a connection that includes means for scanning the concentration ratio of anesthetic set by the vaporizer and the type of anesthetic which is associated with it. This information along with superimposed information provided by a setting device, is communicated to a metering and control unit for setting the vaporizer in accordance with the anesthetic to be used. All of this information is picked up by a scanning device which is associated with the anesthetic device.

A further object of the invention is to provide a device for scanning the supply of a vaporizer so as to insure the vaporizer itself is properly provided with the necessary anesthetic type and that dispensing of the anesthetic is in accordance with the programmed arrangement set by a scanning device under the control of a metering and control unit.

A further object of the invention is to provide a scanning device for anesthetic which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which preferred embodiments of the invention are illustrated.

DETAILED DESCRIPTION OF THE PREFERRED EMBODIMENTS

Referring to the drawings in particular, the invention embodied therein as shown in FIG. 1 to 7 comprises an anesthetic vaporizer 1, which is provided with apparatus for monitoring the dispensing of the anesthetic and which includes a setting device 2 for indicating desired concentration ratios visually and in a code to the anesthetic device 4. The setting device 2 has a connection to the vaporizer for actuating the vaporizer to dispense a selected amount of vaporized anesthetic and a mixing means 31 associated therewith for mixing the proper concentration ratio of anesthetic and fresh gas to be dispensed. A scanning device 12 is provided for scanning the code from the setting device. A metering and control device 9 is connected to the scanning device. A metering and control unit 9 controls the remote setting device 30 which in turn controls the mixing means 31. In this embodiment the metering and control unit 9 controls the concentration ratio in accordance with the indicated ratio of the setting device 2 and any other information such as the type, temperature and pressure of the gases. The anesthetics device 4 includes a support 5 for the mechanical coupling of the vaporizer 1.

Figure 1:
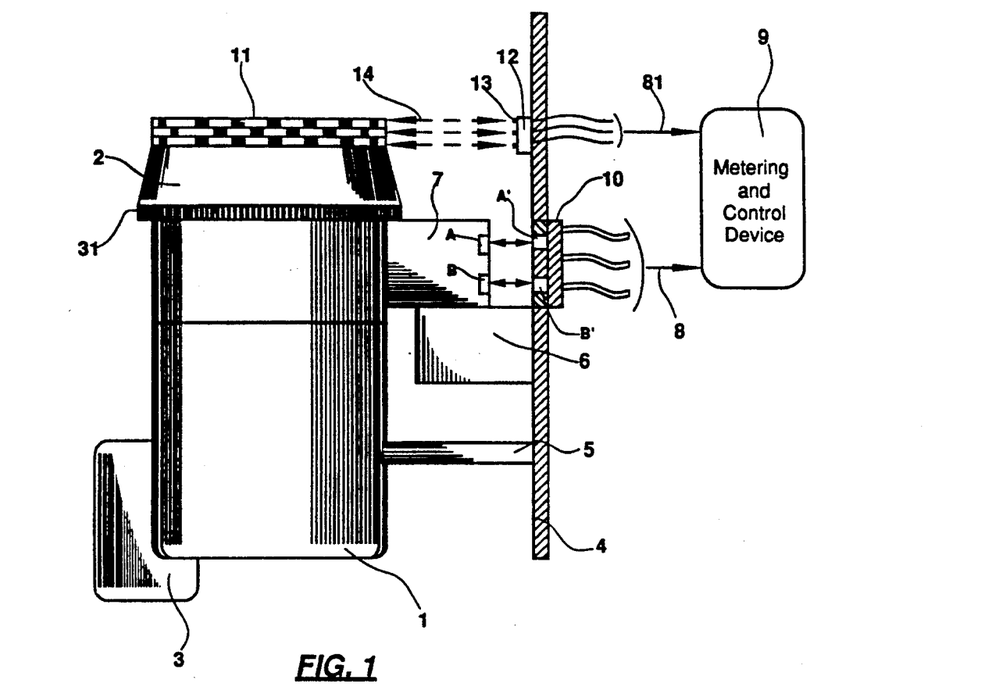
FIG. 1 is a schematic perspective view, partly in section, showing an anesthetic vaporizer having an anesthetic device connected and constructed in accordance with the invention.

FIG. 1 represents an anesthetic vaporizer 1 with its setting device 2, mixing means 31 and a safety filling or supply port 3 in one embodiment which uses optics for coding the type of anesthetic and vaporizer. Light sources/receivers A', B' and C', along with light reflectors A, B and C are used. The light sources/receivers A', B' and C' which are completely visible in FIGS. 2 are mounted on the anesthetic device 4 and the light reflectors A, B and C are mounted on the vaporizer 1 opposite their respective light sources/ receivers.

The light signals emitted by the light sources/receivers A', B', C' are reflected from the light reflectors corresponding to them and transmitted by signal lines 8 to the metering and control unit 9. Light beams between A' and A, B' and B, C' and C are reflected when A, B, C have a white surface, and are absorbed, when A, B, C have a black surface. When a specific vaporizer, e.g. a vaporizer containing halothane, is put on the receiver block 6, A has a black surface while B and C each have a white surface. This is recognized by the metering and control unit 9 as being the allowed combination for halothane. The light sources/receivers A', B', C' are held on a wall of the housing of the anesthetics device 4 by a mounting plate 10.

For the identification of the selected concentration of the anesthetic, further coding in the shape of three superimposed strips 11 can be provided on the setting device 2, preferably having the shape of a handwheel. Each of these strips has a coding of white and black sections or fields. The coding of the strips 11 is read by a scanning device 12 by lighting the strips 11 by means of additional light sources/receivers 1 facing them. The light beams 14 are reflected when they hit a white surface and are absorbed when they hit a black surface. The resulting signals are fed into the same metering and control unit 9 by means of a signal line 81.

Figure 2:
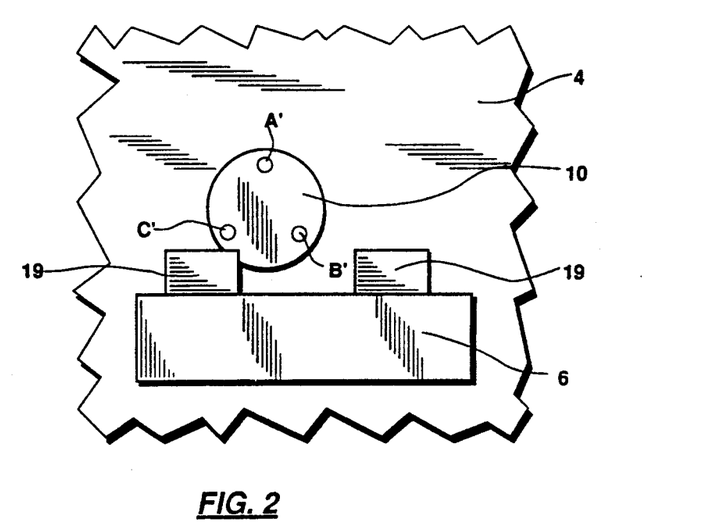
FIG. 2 is a partial end elevational view of the vaporizer shown in FIG. 1 with the anesthetic device removed.

In FIG. 2 a part of the outer surface of the anesthetics device 4 is shown in the area where the reflex light barriers A', B', C' protrude in a triangular arrangement. As the anesthetic vaporizer 1 with its setting device 2 is not mounted, the receiver block 6 with its holding pegs or pins 19 is visible.

Figure 3:
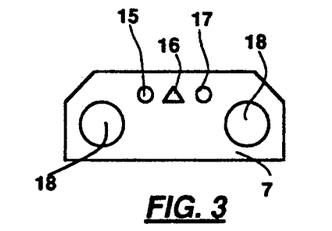
FIG. 3 is a bottom plan view of the holder shown in FIG. 1.

FIG. 3 shows another embodiment of a coding arrangement, wherein the contact surface of the holder 7 has three recesses 15, 16, 17 of various shape and depth. In the edge area of the holder 7 borings 18 are provided for the reception of the two holding pegs 19 of the receiver block 6.

Figure 4:
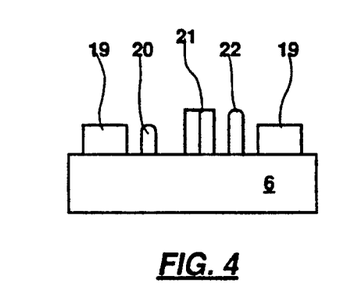
FIG. 4 is a side elevational view of a receiver block shown in FIG. 1.

In the receiver block or plug 6 shown in FIG. 4 the pins 20, 21, 22 corresponding in shape and length to the recesses 15, 16, 17 are mounted between the holding pegs (19).

Figure 5:
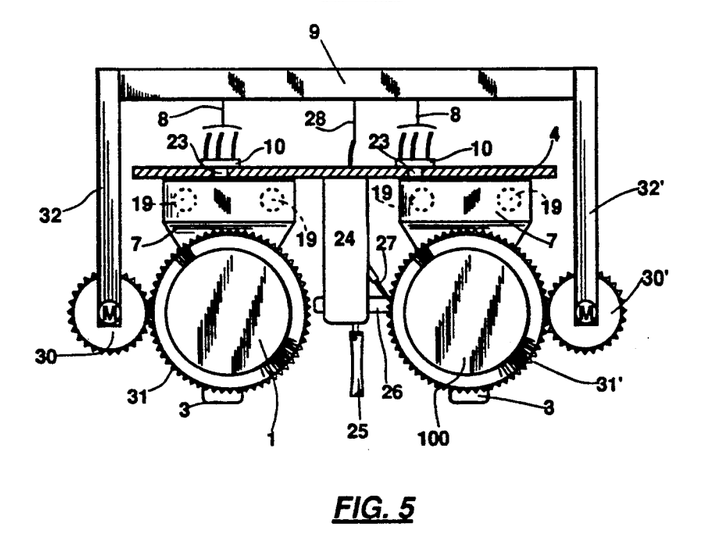
FIG. 5 is a partial horizontal sectional view of another embodiment of the invention showing two anesthetic vaporizers.

FIG. 5 shows a top view of two anesthetic vaporizers 1 and 100, which are held on the respective pegs 19 of the receiver blocks 6 by means of their respective holders 7, the receiver blocks 6 being fastened to the anesthetics device 4. Behind the vaporizers 1, 100 the respective mounting plates 10 are fastened on the inner surface of the fastening wall of the anesthetics device 4. The mounting plates contain the reflex light sources/receivers A', B', and C' embedded in a pattern assigned to the respective vaporizer 1 or 100. The light beams of the light sources/receivers A', B', C' hit the light reflectors A, B, C through the openings 23, the light reflectors being provided on the backs of the holders 7 facing the light sources/receivers A', B', C'. A stopper 24 is arranged between two vaporizers 1 and 100, which has on its face a stop lever 26 which can be actuated by means of a slider 25. The vaporizer 100 cannot be activated when the stop lever 26 is engaged with the setting device 2 of the vaporizer 100. If the stop lever 26 is moved into the other end position, the end of the stop lever 26 is moved out of the range of the light barrier 27 and it receives no reflex light. Its resulting zero signal, e.g. on the signal line 28 shows the blocking of the vaporizer 1 and the release of the vaporizer 100.

Figure 6:
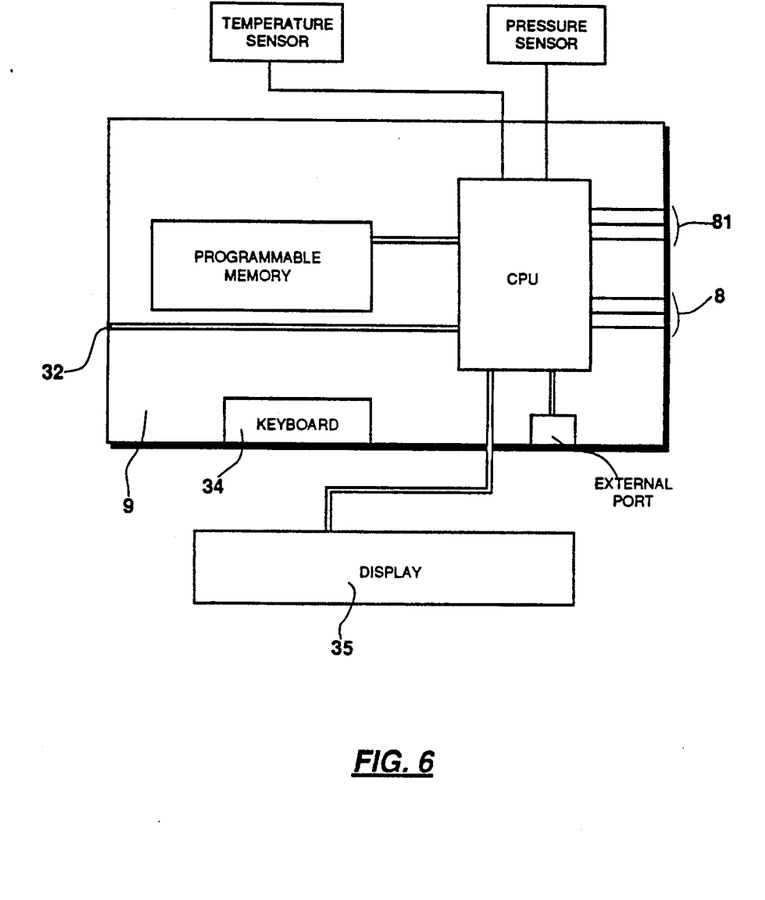
FIG. 6 shows a schematic view of a metering and control unit with a permanent memory, which contains all vaporizer relevant data and a central processing unit (CPU)

FIG. 6 shows a schematic view of the metering and control unit 9 with a permanent memory, which contains all vaporizer relevant data and a central processing unit (CPU). Any change of information may be performed by inserting new information into the memory by means of a keyboard 34. Via display 35 stored information and actual measuring values may be displayed, if desired. The metering an control unit 9 is connected with the remote setting device 30 via signal line 32.

Figure 7:
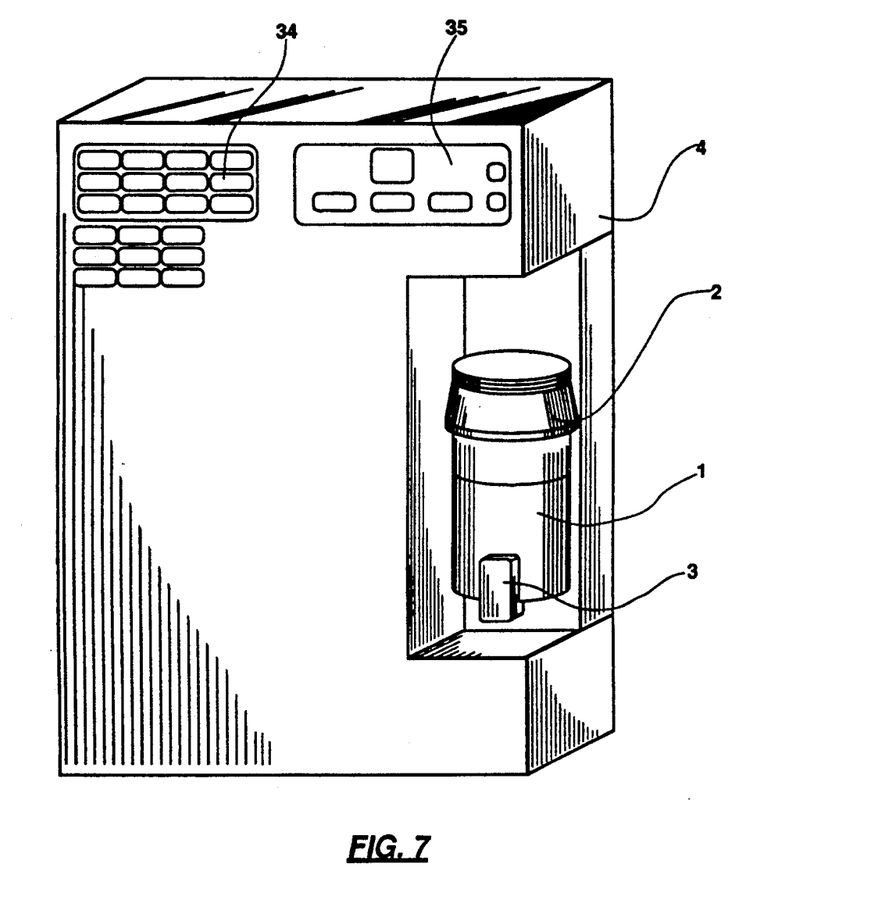
FIG. 7 shows a perspective view of an anesthetics device and a keyboard with a display on a front panel.

FIG. 7 shows a perspective view of the anesthetics device 4 with the keyboard 34 and display 35 on the front panel.

While specific embodiments of the invention have been shown and described in detail to illustrate the application of the principles of the invention, it will be understood that the invention may be embodied otherwise without departing from such principles.

What is claimed is:

1. An anesthetic control device, comprising:
   an anesthetic vaporizer device including an amount of a predetermined anesthetic;
   setting means connected to said anesthetic vaporizer device for setting a predetermined concentration ratio of anesthetic for administration to a patient;
   anesthetic coding means connected to said anesthetic vaporizer device for providing information representing a type of the predetermined anesthetic in said anesthetic vaporizer device;
   anesthetic code receiving means operatively connected to said anesthetic coding means for receiving said information representing said type of predetermined anesthetic in said anesthetic vaporizer device;
   a metering and control unit connected to said anesthetic code receiving means;
   a setting device coding means connected to said setting means for providing a setting code representing information of said concentration ratio of anesthetic being administered by said anesthetic vaporizer device to the patient; and,
   setting code receiving means operatively connected to said setting device coding means for receiving said setting code, said setting code receiving means being connected to said metering and control unit.

2. An anesthetic control device according to claim 1, wherein:
   said anesthetic coding means includes a plug member with a plurality of control form parts having a predetermined shape, and said shape of each of said control form parts cooperating to define said anesthetic coding means;
   said anesthetic code receiving means including a coupling element for coupling with said plug member, said coupling element including recesses for receiving said control form parts; and,
   signal emitter means associated with said coupling element for detecting a presence of said control form parts and providing a signal representing said information to said metering and control unit.

3. An anesthetic control device according to claim 1, further comprising:
   another anesthetic vaporizer device positioned adjacent said anesthetic vaporizer device, said another anesthetic vaporizer device including another setting means;
   a stopping element for engaging said setting means of one of said anesthetic vaporizer device and said another anesthetic vaporizer device for preventing one of said anesthetic vaporizer device and said another anesthetic vaporizer device from providing amounts of anesthetic; and
   detection means for sensing the position of said stopping element and for detecting zero flow of anesthetic from one of said anesthetic vaporizer device and said another anesthetic vaporizer device.

4. An anesthetic control device according to claim 1, wherein:
   said metering and control unit includes a memory for storing and retrieving information corresponding to said anesthetic vaporizer device and the predetermined anesthetic.

5. An anesthetic control device according to claim 4, wherein said metering and control unit is connected to said anesthetic vaporizer device.

6. An anesthetic control device in accordance with claim 4, wherein:
   said metering and control unit also includes a central processing unit for processing said information from said memory and information from said anesthetic code receiving means and setting code receiving means; and
   means for displaying said information from said memory, information from said code receiving means, and setting code receiving means and results of processing by said CPU.

7. An anesthetic control device in accordance with claim 6, further comprising:
   a mixing means on said support for further adjustment of said anesthetic concentration ratio; and
   said metering and control unit also controlling said mixing means.

8. An anesthetic control device, comprising:

An anesthetic vaporizer including an amount of predetermined anesthetic;

an anesthetic device coding means connected to said anesthetic vaporizer for producing a code representing a type and concentration ratio of anesthetic, said coding means including a plug member with a plurality of control form parts having a predetermined shape, said control form parts being shaped pins, with the length of said pins defining said code;

a setting means connected to said anesthetic vaporizer for setting concentration ratios of anesthetic;

a support having a mounting means for holding said anesthetic vaporizer;

an anesthetic device code receiving means on said support for receiving said code, said anesthetic device code receiving means including borings of various depths for receiving said control form parts;

a metering and control unit on said support connected to said anesthetic device code receiving means; and signal emitter means associated with said anesthetic device code receiving means for detecting a presence of said control forms and providing a signal representing said code to said metering and control unit, said signal emitter means including switch elements provided along the depth of said borings for indicating penetration of each of said pins.

9. An anesthetic control device comprising:

a container for anesthetic having a code identifying a predetermined type of anesthetic contained in said container;

setting means connected to said container for setting and displaying a predetermined concentration ratio;

a support for supporting said container;

scanning means on said support for reading said code on said container and for reading said predetermined concentration ratio displayed on said setting means; and a metering and control device on said support, and receiving from said scanning means said anesthetic type and said predetermined concentration ratio.

10. An anesthetic control device, comprising:

an anesthetic vaporizer device including an amount of a predetermined anesthetic;

setting means connected to said anesthetic vaporizer device for setting a predetermined concentration ratio of anesthetic for administration to a patient;

anesthetic coding means connected to said anesthetic vaporizer device for providing information representing a type of the predetermined anesthetic in said anesthetic vaporizer device;

anesthetic code receiving means operatively connected to said anesthetic coding means for receiving said information representing said type of predetermined anesthetic in said anesthetic vaporizer device;

a metering and control unit connected to said anesthetic code receiving means;

a setting device coding means connected to said setting means for providing a setting code representing information of said concentration ratio of anesthetic being administered by said anesthetic vaporizer device to the patient; and, setting code receiving means operatively connected to said setting device coding means for receiving said setting code, said setting code receiving means being connected to said metering and control unit;

wherein said setting means includes a disk-shaped hand wheel indicating the amount of anesthetic provided to said anesthetic vaporizer device, said anesthetic coding means including a digitally coded strip attached to said hand wheel; and said setting code receiving means including a scanning unit for reading code markings on said digitally coded strip.

11. An anesthetic control device, comprising:

an anesthetic vaporizer device including an amount of a predetermined anesthetic;

setting means connected to said anesthetic vaporizer device for setting a predetermined concentration ratio of anesthetic for administration of a patient;

anesthetic coding means connected to said anesthetic vaporizer device for providing information representing a type of the predetermined anesthetic in said anesthetic vaporizer device;

anesthetic code receiving means operatively connected to said anesthetic coding means for receiving said information representing said type of predetermined anesthetic in aid anesthetic vaporizer device;

a metering and control unit connected to said anesthetic code receiving means;

a setting device coding means connected to said setting means for providing a setting code representing information of said concentration ratio of anesthetic being administered by said anesthetic vaporizer device to the patient; and, setting code receiving means operatively connected to said setting device coding means for receiving said setting code, said setting code receiving means being connected to said metering and control unit;

wherein said anesthetic coding means includes light sources, receivers and reflectors; and said anesthetic code receiving means also including light sources and receivers.

* * * * *

UNITED STATES PATENT AND TRADEMARK OFFICE
CERTIFICATE OF CORRECTION

PATENT NO. : 5,293,865
DATED : March 15, 1994
INVENTOR(S) : Altner et al

It is certified that error appears in the above-identified patent and that said Letters Patent is hereby corrected as shown below:

On title page, item [75] change the Inventors information as follows:

[75] Inventors: Claus-Dieter Brandt, Bad Schwartau

Signed and Sealed this

Twenty-fourth Day of May, 1994

Attest:

BRUCE LEHMAN

Attesting Officer       Commissioner of Patents and Trademarks